(12) United States Patent
Dai

(10) Patent No.: US 7,022,510 B2
(45) Date of Patent: Apr. 4, 2006

(54) HUMAN MEGAKARYOCYTE-ASSOCIATED TYROSINE KINASE (MATK)-RELATED GENE VARIANT ASSOCIATED WITH LUNG CANCERS

(76) Inventor: Ken-Shwo Dai, 1F., No. 18, Industry E. Rd., IV, Science-Based Industrial Park, Hsinchu (TW)

( * ) Notice: Subject to any disclaimer, the term of this patent is extended or adjusted under 35 U.S.C. 154(b) by 0 days.

(21) Appl. No.: 10/996,021

(22) Filed: Nov. 23, 2004

(65) Prior Publication Data

US 2005/0136461 A1    Jun. 23, 2005

Related U.S. Application Data

(62) Division of application No. 10/103,380, filed on Mar. 21, 2002, now Pat. No. 6,908,755.

(51) Int. Cl.
*C07H 21/04* (2006.01)
*C12N 1/20* (2006.01)
*C12N 15/00* (2006.01)
*C12N 9/12* (2006.01)
*C12Q 1/68* (2006.01)

(52) U.S. Cl. .............. 435/252.3; 435/320.1; 435/6; 435/194; 536/23.2

(58) Field of Classification Search ............... 536/23.2; 435/252.3, 320.1, 194, 6
See application file for complete search history.

(56) References Cited

OTHER PUBLICATIONS

Sethi, T. "Science, medicine, and the future: Lung cancer" *BMJ*, 314 (7081): 652, (1997).

Sekido, Y., et al. "Preferential Expression of c-*kit* Protooncogene Transcripts in Small Cell Lung Cancer" *Cancer Research*, vol. 51, p. 2416-2419, (1991).

Wang, L., et al. "C-CAM1, a Candidate Tumor Suppressor Gene, Is Abnormally Expressed in Primary Lung Cancers" *Clinical Cancer Research*, vol. 6, p. 2988-2993, (2000).

Avraham, S., et al., "Structural and Functional Studies of the Intracellular Tyrosine Kinase MATK Gene and Its Translated Product" *J. of Biological Chemistry*, vol. 270, No. 4, p. 1833-1842, (1995).

Yamaguchi, N., et al. "Overexpression of the Csk homologous kinase (Chk tyrosine kinase) induces multinucleation: a possible role for . . . dynamics" *J. of Cell Science*, vol. 114, p. 1631-1641, (2001).

Jhun, B.H., et al. "The MATK Tyrosine Kinase Interacts in a Specific and SH2-dependent Manner with c-Kit" *J. of Biological Chemistry*, vol. 270, p. 16, p. 9661-9666, (1995).

Price, D.J., et al. "Direct Association of Csk Homologous Kinase (CHK) with the Diphosphorylated Site $Tyr^{568/570}$ of . . . Megakaryocytes" *J. of Biological Chemistry*, vol. 272, No. 9, p. 5915-5920, (1997).

*Primary Examiner*—Maryam Monshipouri
(74) *Attorney, Agent, or Firm*—Ladas & Parry LLP

(57) ABSTRACT

The invention relates to the nucleic acid of a novel human MATK-related variant (MATKV) and the polypeptides encoded thereby. The invention also provides a process for producing the polypeptide encoded by MATKV. The invention further provides the uses of the nuclei acid of MATKV and the polypeptide encoded thereby in diagnosing the disease associated with the deficiency of human MATK gene, in particular lung cancers, preferably small cell lung cancers.

4 Claims, 16 Drawing Sheets

FIG.1A

```
GGAGCAACTCGCTCCAAGTTGTGCAGCCCGGACCGCCTCGGGGTGTGCAGCCGGTCGCG         60
GAGGCCCTCCTGGGGGCGGGGCTCGGGGCGCGGGGCCCCTGAGCAGAAAACAGG           120
AAGAACCAGGCTCGGTCCAGTGGCACCTCCTAGCTCCTCCCTGTGCCAGCCGCTGGCC        180
TGTGGGCAGCCATTCCCAGCGTCCCCGACTGTGACCACTTGCTCAGTGTGCCTCTCACCT      240
GCCTCAGTTCCCTCTGGGGCGGGGCGAGGCTCTGGTTTCCTGGCGGGCATT               300
                M   A   G   R   G   S   L   V   S   W   R   A   F    13
TCACGGGCTGTGATTCTGCTGAGGAACTTCCCCGGTGAGCCCGCTTCCTCCGAGCCTG       360
 H   G   C   D   S   A   E   E   L   P   R   V   S   P   R   F   L   R   A   W    33
GCACCCCCTCCCCGTCTCAGCCAGGATGCCAACGAGGCCCAGGCCGTGGCGTGGCCCCAGTG   420
 H   P   P   V   S   A   R   M   P   T   R   R   W   A   P   G   T   Q   C    53
TATCACCAAATGCGAGCACACCCGCCCCAAGCCCAGGCCTTCCGCAAGGGCGA            480
 I   T   K   C   E   H   T   R   F   K   P   G   E   L   A   F   R   K   G   D    73
CGTGGTCACCATCCTGGAGGCCTGCGAGAACAAGAGCTGGTACCGTCAAGCACCACAC       540
 V   V   T   I   L   E   A   C   E   N   K   S   W   Y   R   V   K   H   H   T    93
CAGTGGACAGGAGAGGGGCTGCTGGCAGGGGCTGCAGCGGCTGCGGGACGGGGAGGCCCTCTCCGC 600
 S   G   Q   E   G   L   L   A   A   G   A   L   R   D   G   E   A   L   S   A   113
```

FIG.1B

```
ACACCCAAGCTCAGCCTCATGCCGTGGTTCCACGGGAAGATCTCGGGCCAGGAGGCTGT  660
 D  P  K  L  S  L  M  P  W  F  H  G  K  I  S  G  Q  E  A  V   133
CCAGCAGCTGCAGCCTCCCGAGGATGGGCTGTTCCTGGTGCGCGAGTCCGCGCGCCACCC  720
 Q  Q  L  Q  P  P  E  D  G  L  F  L  V  R  E  S  A  R  H  P   153
CGGCGACTACGTCCTGTGCGTGAGCTTTGGCCGCGACGTCATCCACTACCGCGTGCTGCA  780
 G  D  Y  V  L  C  V  S  F  G  R  D  V  I  H  Y  R  V  L  H   173
CCGCGACGGCCACCTCACAATCGATGAGGCCGTGTTCTTCTGCAACCTCATGGACATGGT  840
 R  D  G  H  L  T  I  D  E  A  V  F  F  C  N  L  M  D  M  V   193
GGAGAGGCCACCCGGGAACGGAACAGGATGCTGGGGTTCCCCTCCCTGGGCTGGGCTCA   900
 E  R  P  P  G  N  G  T  G  C  W  G  S  P  P  W  G  W  A  H   213
TGGCTGTCCCACCATCCTGCAGCATTACAGCAAGGACAAGGGCGCTATCTGCACCAAGCT  960
 G  C  P  T  I  L  Q  H  Y  S  K  D  K  G  A  I  C  T  K  L   233
GGTGAGACCAAAAGCGGAAACACGGAAGTCGGCCGAGGAGGAGCTGGCCAGGGCCGGGG  1020
 V  R  P  K  R  K  H  G  T  K  S  A  E  E  E  L  A  R  A  G   253
CTGGTTACTGAACCTGCAGCATTTGACACTTCTGGGAGCACAGATCGGAGAGGGAGAGTTTGG 1080
 W  L  N  L  Q  H  L  T  L  G  A  Q  I  G  E  G  E  F  G    273
```

FIG. 1C

```
AGCTGTCCTGCAGGGTGAGTACCTGGGGCAAAAAGTGGCCGTGAAGAATATCAAGTGTGA   1140
 A  V  L  Q  G  E  Y  L  G  Q  K  V  A  V  K  N  I  K  C  D    293
TGTGACAGCCCAGGCCTTCCTGGACGAGACGGCCGTCATGACGAAGATGCAACACGAGAA   1200
 V  T  A  Q  A  F  L  D  E  T  A  V  M  T  K  M  Q  H  E  N    313
CCTGGTGGTCTCCCTGCACGTGGCTGAGGGCATGGAGTACCTGGAGAGCAAGAA         1260
 L  V  R  L  L  G  V  I  L  H  Q  G  L  Y  I  V  M  E  H  V    333
GAGCAAGGGCAACTTGGTGAACTTTCTGCGGACCCGGGGTCGAGCCCTCGTGAACACCGC   1320
 S  K  G  N  L  V  N  F  L  R  T  R  G  R  A  L  V  N  T  A    353
TCAGCTCCTGCAGTTTCTCTGCACGTGGCCGAGGGCATGGAGTACCTGGAGAGCAAGAA   1380
 Q  L  L  Q  F  S  L  H  V  A  E  G  M  E  Y  L  E  S  K  K    373
GCTTGTGCACCGCGACCTGGCCGCCCGCAACATCCTGGTCTCAGAGGACCTGGTGGCCAA   1440
 L  V  H  R  D  L  A  A  R  N  I  L  V  S  E  D  L  V  A  K    393
GGTCAGCGACTTTGGCCTGGCCAAAGCCGAGCGGAAGGGCTAGACTCAAGCCCGGCTGCC   1500
 V  S  D  F  G  L  A  K  A  E  R  K  G  L  D  S  S  R  L  P    413
CGTCAAGTGGACGGCCCCGGAGGCTCTCAAACACGGGTTCACCAGCAAGTCGGATGTCTG   1560
 V  K  W  T  A  P  E  A  L  K  H  G  F  T  S  K  S  D  V  W    433
```

FIG. 1D

```
GAGTTTGGGGTGCTGCTCTGGGAGGTCTTCTCATATGGACGGGCTTCCGTACCCTAAAAT  1620
 S  F  G  V  L  L  W  E  V  F  S  Y  G  R  A  P  Y  P  K  M   453
GTCACTGAAAGAGGTGTCGGAGGCCGTGGAGAAGGGTACCGCATGGAACCCCCGAGGG    1680
 S  L  K  E  V  S  E  A  V  E  K  G  Y  R  M  E  P  P  E  G   473
CTGTCCAGGCCCGTGCACGTCCTCATGAGCAGCTGTGGGAGGCAGAGCCGCCGGCCGG    1740
 C  P  G  P  V  H  V  L  M  S  S  C  W  E  A  E  P  P  A  G   493
CCACCCTTCCGCAAACTGGCCGAGAAGCTACGCGGGAGCTACGCAGTGCAGGTGCCCCA   1800
 H  P  S  A  N  W  P  R  S  W  P  G  S  Y  A  V  Q  V  P  Q   513
GCCTCCGTCTCAGGGCAGGACGCCGAGAGGACCCCGAAGCCCAGAGCCCTGAC         1860
 P  P  S  Q  G  R  T  P  T  V  H  L  A  P  K  P  G  A  L  T   533
CCCACCCGGTGGCCCTTGCCCCAGAGGACCGAGAGAGTGGAGAGTGCGGTGGGGGCA     1920
 P  P  G  G  P  W  P  Q  R  T  E  R  V  E  S  A  A  W  G  H   553
CTGACCAGGCCCAAGGAGGTCCAGGCGGCAAGTCATCCTCCTGGTGCCCACAGCAGGG    1980
GCTGGGCCCACGTAGGGGCTCTGGGGGCGGCCCGTGGACACCCCAGACCTGCGAAGGATGAT 2040
CGCCCGATAAAGACGGATTCTAAGG                                      2065
```

FIG.2A

```
         1                                                            60
MATK    GGAGCAACTCGCTCCAAGTTGTGCAGCCGGACCGCCTCGGGTGTGCAGCCGGTCGCG
MATKV   GGAGCAACTCGCTCCAAGTTGTGCAGCCGGACCGCCTCGGGTGTGCAGCCGGTCGCG 61                                                           120
MATK    GAGGCCCTCCTGGGGGCGGGGGCGGGGGGGCTCGGGGCGCCCCCTGAGCAGAAAACAGG
MATKV   GAGGCCCTCCTGGGGCCTCCCTGGGGGCGGGGGGGCTCGGGGCGCCCCCTGAGCAGAAAACAGG 121                                                          180
MATK    AAGAACCAGGCTCGGTCCAGTGGCACCCCAGCTCCCTACCTCCTGTGCCAGCCGCCTGGCC
MATKV   AAGAACCAGGCTCGGTCCAGTGGCACCCCAGCTCCCTACCTCCTGTGCCAGCCGCCTGGCC 181                                                          240
MATK    TGTGGCAGGCCATTCCCCAGCGTCCCCGACTGTGACCACTTGCTCAGTGTGCCTCTCACCT
MATKV   TGTGGCAGGCCATTCCCTCCCCAGCGTCCCCGACTGTGACCACTTGCTCAGTGTGCCTCTCACCT
```

FIG. 2B

```
        241
MATK    GCCTCAGTTTCCTCTGGGGGCGAGGCTCTCTGGTTTCCTGGCGGGCATT      300
MATKV   GCCTCAGTTTCCTCTGGGGGCGAGGCTCTCTGGTTTCCTGGCGGGCATT

301
MATK    TCACGGCTGTGATTCTGCTGAGGAACTTCCCCGGGTGAGCCCCGCTTCCTCCGAGCCTG   360
MATKV   TCACGGCTGTGATTCTGCTGAGGAACTTCCCCGGGTGAGCCCCGCTTCCTCCGAGCCTG

361
MATK    GCACCCCCCTCCCCGTCTCAGCCAGGATGCCAACGAGGCGCTGGGCCCCGGGCACCCAGTG  420
MATKV   GCACCCCCCTCCCCGTCTCAGCCAGGATGCCAACGAGGCGCTGGGCCCCGGGCACCCAGTG

421
MATK    TATCACCAAATGCGAGCACACCCGCCAAGCCTGGCCTTCCGCAAGGGCGA    480
MATKV   TATCACCAAATGCGAGCACACCCGCCAAGCCTGGCCTTCCGCAAGGGCGA
```

FIG.2C

```
       481                                                            540
MATK   CGTGGTCACCATCCTGGAGGCCTGCGAGAACAAGAGCTGGTACCGCGTCAAGCACCACAC
MATKV  CGTGGTCACCATCCTGGAGGCCTGCGAGAACAAGAGCTGGTACCGCGTCAAGCACCACAC 541                                                            600
MATK   CAGTGGACAGGAGGGGCTGCTGGCAGTGGCGCTGGGGAGGGCCCTCTCCGC
MATKV  CAGTGGACAGGAGGGGCTGCTGGCAGTGGCGCTGGGGAGGGCCCTCTCCGC 601                                                            660
MATK   AGACCCCAAGCTCAGCCTCATGCCGTGGTTCCACGGGAAGATCTCGGGCCAGGAGGCTGT
MATKV  AGACCCCAAGCTCAGCCTCATGCCGTGGTTCCACGGGAAGATCTCGGGCCAGGAGGCTGT 661                                                            720
MATK   CCAGCAGCTGCAGCCTCCCGAGGATGGGCTGTTCCTGGTGCGGGAGTCCGGCCGCCACCC
MATKV  CCAGCAGCTGCAGCCTCCCGAGGATGGGCTGTTCCTGGTGCGGGAGTCCGGCCGCCACCC
```

FIG.2D

```
       721                                                          780
MATK   CGGCGACTACGTCCTGTGCGTGAGCTTTGGCCGGACGTCATCCACTACGGCGTGCTGCA
MATKV  CGGCGACTACGTCCTGTGCGTGAGCTTTGGCCGCGACGTCATCCACTACCGGCGTGCTGCA 781                                                          840
MATK   CCCGCGACGGGCCACCTCACAAATCGATGAGGCCGTGTTCTTCTGCAACCTCATGGACATGGT
MATKV  CCGCGACGGCCACCTCACACAATCGATGAGGCCGTGTCTCTGCAACCTCATGGACATGGT 841                                                          900
MATK   GGAG---------------------------------------------------------
MATKV  GGAGAGGCCCACCCGGAACGGAACAGGATGCTGGGGTTCCCCTCCCCTGGGGCTCA 901                                                          960
MATK   ------------CATTACAGCAAGGACAAGGGCTATCTGCACCAAGCT
MATKV  TGGCTGTCCCACCATCCTGCAGCATTACAGCAAGGACAAGGGCTATCTGCACCAAGCT
```

FIG.2E

```
       961
MATK   GGTGAGACCAAAGCGGAAACACGGGACCAAGTCGGCCGAGGAGAGCTGGCCAGGGCGGG      1020
MATKV  GGTGAGACCAAAGCGGAAACACGGGACCAAGTCGGCCGAGGAGAGCTGGCCAGGGCGGG

1021
MATK   CTGGTTACTGAACCTGCAGCATTTGACATTGGGAGCACAGATCGGAGAGGGAGAGTTTGG    1080
MATKV  CTGGTTACTGAACCTGCAGCATTTGACATTGGGAGCACAGATCGGAGAGGGAGAGTTTGG

1081
MATK   AGCTGTCCTGCAGGGTGAGTACCTGGGGCAAAAGGTGGCCGTGAAGAATATCAAGTGTGA    1140
MATKV  AGCTGTCCTGCAGGGTGAGTACCTGGGGCAAAAGGTGGCCGTGAAGAATATCAAGTGTGA

1141
MATK   TGTGACAGCCCAGGCCTTCCTGGACGAGACGGCCGTCATGACGAAGATGCAACACGAGAA    1200
MATKV  TGTGACAGCCCAGGCCTTCCTGGACGAGACGGCCGTCATGACGAAGATGCAACACGAGAA
```

FIG. 2F

```
1201
MATK   CCTGGTGCGTCTCCTGGGCGTGATCCTGCACCAGGGCTGTACATTGTCATGGAGCACGT
MATKV  CCTGGTGCGTCTCCTGGGCGTGATCCTGCACCAGGGCTGTACATTGTCATGGAGCACGT
                                                              1260

1261
MATK   GAGCAAGGGCAACCTGTGGTGAACTTTCTGCGGACCCTCGTGAACACCGC
MATKV  GAGCAAGGGCAACCTGTGGTGAACTTTCTGCGGACCCTCGTGAACACCGC
                                                              1320

1321
MATK   TCAGCTCCTGCAGTTTCTCTGCACGTGGCCGAGGGCATGGAGTACCTGGAGAGCAAGAA
MATKV  TCAGCTCCTGCAGTTTCTCTGCACGTGGCCGAGGGCATGGAGTACCTGGAGAGCAAGAA
                                                              1380

1381
MATK   GCTTGTGCACCGCGACCTGGCCCGCCAACATCCTGGTCTCAGAGAGACCTGGTGGCCAA
MATKV  GCTTGTGCACCGCGACCTGGCCCGCCAACATCCTGGTCTCAGAGAGACCTGGTGGCCAA
                                                              1440
```

FIG.2G

```
     1441 GGTCAGGCGACTTTGGCCCTGGCCCAAAGCCGAGCGGAAGGGCTAGACTCAAGCCGGCTGCC    1500
MATK
MATKV GGTCAGGCGACTTTGGCCCTGGCCCAAAGCCGAGCGGAAGGGCTAGACTCAAGCCGGCTGCC

1501 CGTCAAGTGGACGGCGCCCGAGGCTCTCAAACACGGGTTCACCAGCAAGTCGGATGTCTG    1560
MATK
MATKV CGTCAAGTGGACGGCGCCCGAGGCTCTCAAACACGGGTTCACCAGCAAGTCGGATGTCTG

1561 GAGTTTTGGGGTGCTGCTCTCTGGGAGGTCTTCTCATATGGACGGGCTCCGTACCCTAAAAT    1620
MATK
MATKV GAGTTTTGGGGTGCTGCTCTCTGGGAGGTCTTCTCATATGGACGGGCTCCGTACCCTAAAAT

1621 GTCACTGAAAGAGAGGTGTCGGAGGCCGTGGAGAAGGGTACCGCATGAACCCCCGAGGG    1680
MATK
MATKV GTCACTGAAAGAGAGGTGTCGGAGGCCGTGGAGAAGGGTACCGCATGAACCCCCGAGGG
```

FIG.2H

```
      1681                                                           1740
MATK   CTGTCCAGGCCCCGTGCACGTCCTCATGAGCAGCTGCTGGGAGGCAGAGAGCCCGCCGG
MATKV  CTGTCCAGGCCCCGTGCACGTCCTCATGAGCAGCTGCTGGGAGGCAGAGAGCCCGCCGG 1741                                                           1800
MATK   CCACCCCTTCCGCAAACTGGCCCGAGAAAGCTGGCCCGGAGCTACGCAGTGCAGGTGCCCCCA
MATKV  CCACCCCTTCCGCAAACTGGCCCGAGAAAGCTGGCCCGGAGCTACGCAGTGCAGGTGCCCCCA 1801                                                           1860
MATK   GCCTCCGTCTCAGGGCAGGACGCCCACCTCGCCCCGAAGCCAGGAGCCCTGAC
MATKV  GCCTCCGTCTCAGGGCAGGACGCCCACCTCGCCCCGAAGCCAGGAGCCCTGAC 1861                                                           1920
MATK   CCCACCCGGTGGCCCTTGGCCCCCAGAGGACCGAGAGAGTGGAGAGTGCGGGCGTGGGGGCA
MATKV  CCCACCCGGTGGCCCTTGGCCCCCAGAGGACCGAGAGAGTGGAGAGTGCGGGCGTGGGGGCA
```

FIG. 2I

```
      1921                                                        1980
MATK   CTGACCAGGCCCAAGGAGGGTCCAGGCCAAGTCATCCTCCTGGTGCCCACAGCAGGG
MATKV  CTGACCAGGCCCAAGGAGGGTCCAGGCCAAGTCATCCTCCTGGTGCCCACAGCAGGG 1981                                                        2040
MATK   GCTGGCCCCACGTAGGGGCTCTGGGCCCGTGGACACCCCAGACCTGCGAAGGATGAT
MATKV  GCTGGCCCCACGTAGGGGCTCTGGGCCCGTGGACACCCCAGACCTGCGAAGGATGAT

2041
MATK   CGCCCGATAAAGACGGATTCTAAGG     1987
MATKV  CGCCCGATAAAGACGGATTCTAAGG     2065
```

FIG.3A

```
1    MATK  MAGRGSLVSWRAFHGCDSAEELPRVSPRFLRAWHPPPVSARMPTRRWAPGTQCITKCEHT      60
     MATKV MAGRGSLVSWRAFHGCDSAEELPRVSPRFLRAWHPPPVSARMPTRRWAPGTQCITKCEHT

61   MATK  RPKPGELAFRKGDVVTILEACENKSWYRVKHHTSGQEGLLAAGALRDGEALSADPKLSLM     120
     MATKV RPKFGELAFRKGDVVTILEACENKSWYRVKHHTSGQEGLLAAGALRDGEALSADPKLSLM

121  MATK  PWFHGKISGQEAVQQLQPPEDGLFLVRESARHPGDYVLCVSFGRDVIHYRVLHRDGHLTI     180
     MATKV PWFHGKISGQEAVQQLQPPEDGLFLVRESARHPGDYVLCVSFGRDVIHYRVLHRDGHLTI

181  MATK  DEAVFFCNLMDMVE------------------HYSKDKGAICTKLVRPKRKH             240
     MATKV DEAVFFCNLMDMVERPPGNGTGCWGSPPWGWAHGCPTILQHYSKDKGAICTKLVRPKRKH
```

FIG.3B

```
     241                                                        300
MATK  GTKSAEEELARAGWLLNLQHLTLGAQIGEGEFGAVLQGEYLGQKVAVKNIKCDVTAQAFL
MATKV GTKSAEEELARAGWLLNLQHLTLGAQIGEGEFGAVLQGEYLGQKVAVKNIKCDVTAQAFL 301                                                        360
MATK  DETAVMTKMQHENLVRLLGVILHQGLYIVMEHVSKGNLVNFLRTRGRALVNTAQLLQFSL
MATKV DETAVMTKMQHENLVRLLGVILHQGLYIVMEHVSKGNLVNFLRTRGRALVNTAQLLQFSL 361                                                        420
MATK  HVAEGMEYLESKKLVHRDLAARNILVSEDLVAKVSDFGLAKAERKGLDSSRLPVKWTAPE
MATKV HVAEGMEYLESKKLVHRDLAARNILVSEDLVAKVSDFGLAKAERKGLDSSRLPVKWTAPE 421                                                        480
MATK  ALKHGFTSKSDVWSFGVLLMEVFSYGRAPYPKMSLKEVSEAVEKGYRMEPPEGCPGPVHV
MATKV ALKHGFTSKSDVWSFGVLLMEVFSYGRAPYPKMSLKEVSEAVEKGYRMEPPEGCPGPVHV
```

FIG.3C

```
481  LMSSCWEAEPPAGHPSANWPRSWPGSYAVQVFQPPSQGRTPTVHLAPKPGALTPPGGPWP  540
MATK   LMSSCWEAEPPAGHPSANWPRSWPGSYAVQVFQPPSQGRTPTVHLAPKPGALTPPGGPWP
MATKV  LMSSCWEAEPPAGHPSANWPRSWPGSYAVQVFQPPSQGRTPTVHLAPKPGALTPPGGPWP

541  QRTERVESAAWGH  527
MATK   QRTERVESAAWGH
MATKV  QRTERVESAAWGH  553
```

HUMAN MEGAKARYOCYTE-ASSOCIATED TYROSINE KINASE (MATK)-RELATED GENE VARIANT ASSOCIATED WITH LUNG CANCERS

This is a Divisional of U.S. application Ser. No. 10/103,380 filed on Mar. 21, 2002 now U.S. Pat. No. 6,908,755 issued Jun. 21, 2005.

FIELD OF THE INVENTION

The invention relates to the nucleic acid of a novel megakaryocyte-associated tyrosine kinase (MATK)-related gene variant, the polypeptide encoded thereby, the preparation process thereof, and the uses of the same in diagnosing diseases associated with the deficiency of human MATK gene, in particular, lung cancers.

BACKGROUND OF THE INVENTION

Lung cancer is one of the major causers of cancer-related deaths in the world. There are two primary types of lung cancers: small cell lung cancer (SCLC) and non-small cell lung cancer (NSCLC) (Carney, (1992a) Curr. Opin. Oncol. 4:292–8). Small cell lung cancer accounts for approximately 25% of lung cancer and spreads aggressively (Smyth et al. (1986) Q J Med. 61: 969–76; Carney, (1992b) Lancet 339: 843–6). Non-small cell lung cancer represents the majority (about 75%) of lung cancer and is further divided into three main subtypes: squamous cell carcinoma, adenocarcinoma, and large cell carcinoma (Ihde and Minna, (1991) Cancer 15: 105–54). In recent years, much progress has been made toward understanding the molecular and cellular biology of lung cancers. Many important contributions have been made by the identification of several key genetic factors associated with lung cancers. However, the treatments of lung cancers still mainly depend on surgery, chemotherapy and radiotherapy. This is because the molecular mechanisms underlying the pathogenesis of lung cancers remain largely unclear.

A recent hypothesis suggests that lung cancer is caused by genetic mutations of at least 10 to 20 genes (Sethi, (1997) BMJ. 314: 652–655). One of the future strategies for the prevention and treatment of SCLC will be focused on the elucidation of the genes associated with protooncogene, in particular, the c-kit gene. This suggestion is based on the evidence that the c-kit gene was found to be expressed preferentially in SCLC (Sekido et al. (1991) Cancer Res 51:2416–9), which indicates an important role of the c-kit gene in the tumorigenic process of SCLC. One of the genes associated with the c-kit is the megakaryocyte-associated tyrosine kinase (MATK) (Jhun et al. (1995) J Biol Chem 270: 9661–6; Price et al. (1997) J Biol Chem 272:5915–20). MATK, a protein tyrosine kinase containing the Src homology 2 and 3 (SH2 and SH3) domains, was also termed Csk-homologous kinase (CHK) based on its high sequence similarity to the Csk tyrosine kinase. The functional roles of MATK have been shown to be involved in cell proliferation and differentiation, and chromosome dynamics (Avraham et al. (1995) J Biol Chem 270:1833–42; Zrihan-Licht et al. (1998) J Biol Chem 273:4065–72; Yamashita et al. (1999) J Biol Chem 274:15059–65; Yamaguchi et al. (2001) J Cell Sci 114:1631–41). The genetic localization analysis has assigned MATK to chromosome 19p13.3 (Avraham et al. (1995) J Biol Chem 270:1833–42). Several studies have shown that the abnormality of chromosome 19 is associated with lung tumor susceptibility (Johansson et al. (1995) Cancer Genet Cytogenet 80:85–6; Dang et al. (2000) J Natl Cancer Inst 92:1355–7; Wang et al. (2000) Clin Cancer Res 6:2988–93; Sobottka et al. (2000) J Neurooncol 49:187–95). Interestingly, the gene variants of a chromosome 19 gene, C-CAM1, were shown to be involved in lung tumorigenesis (Wang et al. (2000) Clin Cancer Res 6:2988–93) raising the possibility that the gene variants of MATK may also be involved in the tumorigenic process of SCLC. Therefore, it is believed that the discovery of gene variants of MATK may serve as important targets for diagnostic markers of SCLC.

SUMMARY OF THE INVENTION

The present invention provides a MATK-related gene variant (MATKV) present in human SCLC tissues. The nucleic acid of MATKV and the polypeptide encoded thereby can be used for the diagnosis of diseases associated with the deficiency of human MATK gene, in particular lung cancers, preferably SCLC.

The invention further provides an expression vector and host cell for expressing MATKV.

The invention further provides a method for producing the polypeptide encoded by MATKV.

The invention further provides an antibody specifically binding to the polypeptide encoded by MATKV.

The invention also provides methods for diagnosing diseases associated with the deficiency of human MATK gene, in particular, lung cancers.

BRIEF DESCRIPTION OF THE DRAWINGS

FIG. 1A to 1D show the nucleotide sequence of MATKV (SEQ ID NO:1) and the corresponding amino acid sequence thereof (SEQ ID NO:2).

FIG. 2A to 2I show the nucleotide sequence alignment between human MATK gene and MATKV.

FIG. 3A to 3C show the amino acid sequence alignment between human MATK protein and the polypeptide encoded by MATKV.

DETAILED DESCRIPTION OF THE INVENTION

According to the present invention, all technical and scientific terms used have the same meanings as commonly understood by persons skilled in the art.

The term "antibody," as used herein, denotes intact molecules (a polypeptide or group of polypeptides) as well as fragments thereof, such as Fab, R(ab')$_2$, and Fv fragments, which are capable of binding the epitopic determinutesant. Antibodies are produced by specialized B cells after stimulation by an antigen. Structurally, antibody consists of four subunits including two heavy chains and two light chains. The internal surface shape and charge distribution of the antibody binding domain are complementary to the features of an antigen. Thus, antibody can specifically act against the antigen in an immune response.

The term "base pair (bp)," as used herein, denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)," as used herein, denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA," as used herein, denotes nucleic acids that synthesized from a MRNA template using reverse transcriptase.

The term "cDNA library," as used herein, denotes a library composed of complementary DNAs which are reverse-transcribed from mRNAs.

The term "complement," as used herein, denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion," as used herein, denotes a removal of a portion of one or more amino acid residues/nucleotides from a gene.

The term "expressed sequence tags (ESTs)," as used herein, denotes short (200 to 500 base pairs) nucleotide sequence that derives from either 5' or 3' end of a cDNA.

The term "expression vector," as used herein, denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell," as used herein, denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition," as used herein, denotes the addition of a portion of one or more amino acid residues/nucleotides to a gene.

The term "in silico," as used herein, denotes a process of using computational methods (e.g., BLAST) to analyze DNA sequences.

The term "polymerase chain reaction (PCR)," as used herein, denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "protein" or "polypeptide," as used herein, denotes a sequence of amino acids in a specific order that can be encoded by a gene or by a recombinant DNA. It can also be chemically synthesized.

The term "nucleic acid sequence" or "polynucleotide," as used herein, denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)," as used herein, denotes a process which transcribes MRNA to complementary DNA strand using reverse transcriptase followed by polymerase chain reaction to amplify the specific fragment of DNA sequences.

The term "transformation," as used herein, denotes a process describing the uptake, incorporation, and expression of exogenous DNA by prokaryotic host cells.

The term "transfection," as used herein, a process describing the uptake, incorporation, and expression of exogenous DNA by eukaryotic host cells.

The term "variant," as used herein, denotes a fragment of sequence (nucleotide or amino acid) inserted or deleted by one or more nucleotides/amino acids.

In the first aspect, the present invention provides the polypeptide encoded by a novel human MATK-related gene variant (MATKV) and the fragments thereof, as well as the nucleic acid of MATKV.

According to the present invention, human MATK cDNA sequence was used to query the human lung EST databases (a normal lung, a large cell lung cancer, and a small cell lung cancer) using BLAST program to search for MATK-related gene variants. One human cDNA partial sequences (i.e., EST) showing similarity to MATK was identified from ESTs deposited in the SCLC database. The cDNA clone, named MATKV (MATK gene variant), was then isolated from the SCLC cDNA library and sequenced. FIGS. 1A to 1D show the nucleotide sequence (SEQ ID NO: 1) of MATKV and its corresponding amino acid sequence (SEQ ID NO: 2).

The full-length of the MATKV cDNA is a 2065 bp clone containing a 1659 bp open reading frame (ORF) extending from 263 bp to 1921 bp, which corresponds to an encoded protein of 553 amino acid residues with a predicted molecular mass of 61.2 kDa. The sequence around the initiation ATG codon of MATKV (located at nucleotide 263 to 265 bp) was matched to the Kozak consensus sequence (A/GC-CATGG) (Kozak, (1987) Nucleic Acids Res. 15: 8125–48; Kozak, (1991) J Cell Biol. 115: 887–903.). To determine the variation in sequence of MATKV cDNA clone, an alignment of MATK nucleotide/amino acid sequence with MATKV was performed (FIGS. 2 and 3). One major genetic insertion was found in the aligned sequences, which shows that MATKV contains a 78 bp insertion in the sequence of human MATK gene from nucleotides 844 to 845. This 78 bp insertion is positioned from nucleotides 845 to 922 of the nucleotide sequence of MATKV, which encode the amino acids 195 to 220 of SEQ ID NO: 2.

In the present invention, a search of ESTs deposited in dbEST (Boguski et al. (1993) Nat Genet. 4: 332–3) at National Center for Biotechnology Information (NCBI) was performed to determine the tissue distribution of MATKV in silico. The result of in silico Northern analysis showed that three ESTs (GenBank accession number BE795492; BE791829; BE791472) were found to confirm the addition of 78 bp nucleotide sequence inserted on the MATKV. These ESTs were generated from the SCLC CDNA library, which suggests that the addition of 78 bp nucleotide fragment located between nucleotides 845 to 922 of MATKV may serve as a useful marker for diagnosing SCLC. Therefore, any nucleotide fragments comprising nucleotides 845 to 922 of MATKV may be used as probes for determining the presence of MATKV under high stringency conditions. An alternative approach is that any set of primers for amplifying the fragment containing nucleotides 845 to 922 of MATKV may be used for determining the presence of human MATK-related gene variant.

Scanning the MATKV sequence against the profile entries in PROSITE (ScanProsite) indicated that MATKV protein contains two N-glycosylation sites (83–86aa and 199–202aa), eight protein kinase C phosphorylation sites (9–11aa, 26–28aa, 39–41aa, 44–46aa, 149–151aa, 371–373aa, 409–411aa, and 427–429aa), seven casein kinase II phosphorylation sites (18–21aa, 55–58aa, 76–79aa, 94–97aa, 128–131aa, 179–182aa, and 244–247aa), eleven N-myristoylation sites (5–10aa, 15–20aa, 98–103aa, 198–203aa, 227–232aa, 241–246aa, 264–269aa, 282–287aa, 336–341aa, 398–403aa, and 406–411aa), one protein kinases ATP-binding region signature (267–288aa), and one tyrosine protein kinases specific active-site signature (374–386aa). A search of the MATKV sequence against the protein profile databases (ProfileScan) indicated that MATKV protein contains one src homology 3 (SH3) domain (58–110aa), one Src homology 2 (SH2) domain (122–194aa), one proline-rich region (470–540aa), and one protein kinase domain (261–540aa).

According to the present invention, the polypeptide encoded by MATKV and the fragments thereof may be produced through genetic engineering techniques. For instance, they may be produced by using appropriate host cells which have been transformed with recombinant DNAs that code for the desired polypeptides or fragments thereof. The nucleotide sequence of MATKV or the fragments thereof is inserted into an appropriate expression vector, i.e., a vector which contains the necessary elements for the transcription and translation of the inserted coding sequence in a suitable host. The nucleotide sequence is inserted into the vector in a manner such that it will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing the sequence of MATKV and appropriate transcriptional/translational control elements. These methods may include in vitro recombinant DNA and synthetic techniques, and in vivo genetic recombinant techniques. (See, e.g., Sambrook, J. Cold Spring Harbor Press, Plainview N.Y., Ch. 4, 8, and 16–17; Ausubel, R. M. et al. (1995) Current protocols in Molecular Biology, John Wiley & Sons, New York N.Y., ch. 9, 13, and 16.)

A variety of expression vector/host systems may be utilized to express MATKV. These include, but not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and more preferably, the bacterium is E. coli.

Alternatively, the polypeptide encoded by MATKV or the fragments thereof may be synthesized using chemical methods. For example, peptide synthesis can be performed using various solid-phase techniques (Roberge, J. Y. et al. (1995) Science 269: 202 to 204). Automated synthesis may be achieved using the ABI 431A peptide synthesizer (Perkin-Elmer).

According to the present invention, the fragments of the nucleic acid of MATKV and the polypeptide encoded thereby are used as primers or probes and immunogens, respectively. Preferably, the purified fragments are used. The fragments may be produced by enzyme digestion, chemical cleavage of isolated or purified polypeptide or nucleotide sequences, or chemical synthesis, and then may be isolated or purified. Such isolated or purified fragments of the polypeptides and nucleotide sequences can be used directed as immunogens and primers or probes, respectively.

The present invention further provides the antibodies which specifically bind to one or more out-surface epitopes of the polypeptide encoded by MATKV.

According to the present invention, immunization of mammals with immunogens described herein, preferably humans, rabbits, rats, mice, sheep, goats, cows, or horses, is performed by following the procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. Nos. 4,271,145 and 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides or fragments thereof may also be generated. For example, such fragments include, but are not limited to, F(ab')$_2$ fragments produced by pepsin digestion of the antibody molecule and Fab fragments generated by reducing the disulfide bridges of the F(ab')$_2$ fragments., Many gene variants have been found to be associated with diseases (Stallings-Mann et al., (1996) Proc Natl Acad Sci USA 93: 12394–9; Liu et al., (1997) Nat Genet 16:328–9; Siffert et al., (1998) Nat Genet 18: 45 to 8; Lukas et al., (2001) Cancer Res 61: 3212 to 9). Since MATKV clone was isolated from SCLC cDNA library and its expression in SCLC was confirmed by in silico Northern analysis, it suggests that MATKV may serve as marker for the diagnosis of diseases associated with the deficiency of human MATK gene, in particular lung cancers, e.g. human SCLC. Thus, the expression level of MATKV relative to MATK may be a useful indicator for screening of patients suspected of having such diseases, and the index of relative expression level (mRNA or protein) may confer an increased susceptibility to the same.

Accordingly, the subject invention further provides methods for diagnosing the diseases associated with the deficiency of human MATK gene in a mammal, in particular, lung cancers, preferably the SCLC.

The method for diagnosing the diseases associated with the deficiency of human MATK gene may be performed by detecting the nucleotide sequence of the MATKV of the invention, which comprises the steps of: (1) extracting the total RNA of cells obtained from the mammal; (2) amplifying the RNA by reverse transcriptase-polymerase chain reaction (RT-PCR) with a set of primers to obtain a cDNA comprising the fragments comprising nucleotides 845 to 922 of SEQ ID NO: 1; and (3) detecting whether the cDNA is obtained. If necessary, the amount of the obtained CDNA sample may be determined.

In this embodiment, one of the primers may be designed to have a sequence comprising the nucleotides of SEQ ID NO: 1 containing nucleotides 845 to 922, and the other may be designed to have a sequence complementary to the nucleotides of SEQ ID NO: 1 at any other locations downstream of nucleotide 922. Alternatively, one of the primers may be designed to have a sequence complementary to the nucleotides of SEQ ID NO: 1 containing nucleotides 845 to 922, and the other may be designed to have a sequence comprising the nucleotides of SEQ ID NO: 1 at any other locations upstream of nucleotide 845. In this case, only MATKV will be amplified.

Alternatively, one of the primers may be designed to have a sequence comprising the nucleotides of SEQ ID NO: 1 upstream of nucleotide 844 and the other may be designed to have a sequence complementary to the nucleotides of SEQ ID NO: 1 downstream of nucleotide 923. Alternatively, one of the primers may be designed to have a sequence complementary to the nucleotides of SEQ ID NO: 1 upstream of nucleotide 844 and the other may be designed to have a sequence comprising the nucleotides of SEQ ID NO: 1 downstream of nucleotide 923. In this case, both MATK and MATKV will be amplified. The length of the PCR fragment from MATKV will be 78 bp longer than that from MATK.

Preferably, the primer of the invention contains 15 to 30 nucleotides.

Total RNA may be isolated from patient samples by using TRIZOL reagents (Life Technology). Tissue samples (e.g., biopsy samples) are powdered under liquid nitrogen before homogenization. RNA purity and integrity are assessed by absorbance at 260/280 nm and by agarose gel electrophoresis. The set of primers designed to amplify the expected sizes of specific PCR fragments of MATKV can be used. PCR fragments are analyzed on a 1% agarose gel using five microliters (10%) of the amplified products. To determine the expression levels for each gene variants, the intensity of the PCR products may be determined by using the Molecular Analyst program (version 1.4.1; Bio-Rad).

The RT-PCR experiment may be performed according to the manufacturer instructions (Boehringer Mannheim). A 50 µl reaction mixture containing 2 µl total RNA (0.1 µg/µl), 1 µl each primer (20 pM), 1 µl each dNTP (10 mM), 2.5 µl DTT solution (100 mM), 10 µl 5X RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

Another embodiment of the method for diagnosing the diseases associated with the deficiency of human MATK gene of the invention may be performed by detecting the nucleotide sequence of MATKV, which comprises the steps of: (1) extracting total RNA from a sample obtained from the mammal; (2) amplifying the RNA by reverse transcriptase-polymerase chain reaction (RT-PCR) to obtain a cDNA sample; (3) bringing the cDNA sample into contact with the nucleic acid of SEQ ID NO: 1 or the fragments thereof; and (4) detecting whether the cDNA sample hybridizes with the nucleic acid. If necessary, the amount of the hybridized sample may be determined.

The expression of gene variants can also be analyzed using Northern blot hybridization approach. Specific fragments comprising nucleotides 845 to 922 of the MATKV may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hr. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variants (cDNAs or PCR) can be detected using microarray approach. The cDNAs or PCR products corresponding to the nucleotide sequences of the invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the invention, the method for diagnosing the diseases associated with the deficiency of human MATK gene may also be performed by detecting the polypeptides encoded by the MATKV of the invention. For instance, the polypeptide in protein samples obtained from the mammal may be determined by, but not limited to, the immunoassay wherein the antibodies specifically binding to the polypeptides of the invention is contacted with the sample, and the antibody-polypeptide complex is detected. If necessary, the amount of antibody-polypeptide complex can be determined.

The polypeptides encoded by MATKV may be expressed in prokaryotic cells by using suitable prokaryotic expression vectors. The CDNA fragments of MATKV may be PCR-amplified using primer set with restriction enzyme digestion sites incorporated in the 5' and 3' ends, respectively. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 h. The bacterially-expressed proteins may be purified.

The polypeptides encoded by MATKV may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5\times10^4$ cells per well. Transfections may be carried out using Lipofectaminutese Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins may be generated using hybridoma technique according to the conventional methods (de StGroth and Scheidegger, (1980) J Immunol Methods 35:1–21; Cote et al. (1983) Proc Natl Acad Sci USA 80: 2026–30; and Kozbor et al. (1985) J Immunol Methods 81:31–42).

According to the invention, the presence of the polypeptides encoded by MATKV in samples of normal lung and lung cancers may be determined by, but not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody specific to the polypeptides encoded by these gene variants. Unbound antibody is removed by washing with TBST for $5\times1$ minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal, SCLC, and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25: 3389–3402; Gish and States, (1993) Nat Genet 3:266–272), at the NCBI with a significance cutoff of $p<10^{-10}$. ESTs representing putative MATKV gene were identified during the course of EST generation.

Isolation of cDNA Clones

One cDNA clone exhibiting EST sequence similar to the MATK gene was isolated from the SCLC cDNA library and named MATKV. The inserts of these clones were subsequently excised in vivo from the λZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect E. coli XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW $IR^2$ DNA sequencing system (LI-COR). Using the primer-walking approach, full-length sequence was determined. Nucleotide and protein searches were performed using BLAST against the non-redundant database of NCBI.

In Silico Tissue Distribution (Northern) Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching to that particular sequence variants (insertions or deletions) with a significance cutoff of $p<10^{-10}$.

References

Altschul et al., Gapped BLAST and PSI-BLAST: a new generation of protein database search programs, Nucleic Acids Res, 25: 3389–3402, (1997).

Ausubel et al., Current protocols in Molecular Biology, John Wiley & Sons, New York N.Y., ch. 9, 13, and 16, (1995).

Avraham et al., Structural and functional studies of the intracellular tyrosine kinase MATK gene and its translated product. J Biol Chem 270:1833–42, (1995).

Boguski et al., dbEST—database for "expressed sequence tags". Nat Genet. 4: 332–3, (1993).

Carney, D. N. The biology of lung cancer. Curr. Opin. Oncol. 4: 292–8, (1992a).

Carney, D. N. Biology of small-cell lung cancer. Lancet 339: 843–6, (1992b).

Cote et al., Generation of human monoclonal antibodies reactive with cellular antigens, Proc Natl Acad Sci USA 80: 2026–30 (1983).

Dang et al., Chromosome 19 translocation, overexpression of Notch3, and human lung cancer. J Natl Cancer Inst 92:1355–7, (2000).

de StGroth and Scheidegger, Production of monoclonal antibodies: strategy and tactics, J Immunol Methods 35:1–21, (1980).

Gish and States, Identification of protein coding regions by database similarity search, Nat Genet, 3:266–272, (1993).

Ihde and Minna, Non-small cell lung cancer. Part II: Treatment. Curr. Probl. Cancer 15: 105–54, (1991).

Jhun et al., The MATK tyrosine kinase interacts in a specific and SH2-dependent manner with c-Kit. J Biol Chem 270:9661–6, (1995).

Johansson et al., Translocation 11; 19 in a mucoepidermoid tumor of the lung. Cancer Genet Cytogenet 80:85–6, (1995).

Kozak, An analysis of 5'-noncoding sequences from 699 vertebrate messenger RNAs. Nucleic Acids Res, 15: 8125–48, (1987).

Kozak, An analysis of vertebrate MRNA sequences: intimations of translational control, J Cell Biol, 115: 887–903, (1991).

Kozbor et al., Specific immunoglobulin production and enhanced tumorigenicity following ascites growth of human hybridomas, J Immunol Methods, 81:31–42 (1985).

Liu et al., Silent mutation induces exon skipping of fibrillin-1 gene in Marfan syndrome. Nat Genet 16:328–9, (1997).

Lukas et al., Alternative and aberrant messenger RNA splicing of the mdm2 oncogene in invasive breast cancer. Cancer Res 61:3212–9, (2001).

Price et al., Direct association of Csk homologous kinase (CHK) with the diphosphorylated site Tyr568/570 of the activated c-KIT in megakaryocytes. J Biol Chem 272: 5915–20, (1997).

Roberge et al., A strategy for a convergent synthesis of N-linked glycopeptides on a solid support. Science 269: 202–4, (1995).

Sambrook, J. Cold Spring Harbor Press, Plainview N.Y., ch. 4, 8, and 16–17.

Sekido et al., Preferential expression of c-kit protooncogene transcripts in small cell lung cancer. Cancer Res 51:2416–9, (1991).

Sethi, Science, medicine, and the future. Lung cancer, BMJ, 314: 652–655, (1997)

Siffert et al., Association of a human G-protein beta3 subunit variant with hypertension. Nat Genet, 18:45–8, (1998).

Smyth et al., The impact of chemotherapy on small cell carcinoma of the bronchus. Q J Med, 61: 969–76, (1986).

Sobottka et al., Frequent loss of heterozygosity at the 19p13.3 locus without LKB1/STK11 mutations in human carcinoma metastases to the brain. J Neurooncol 49:187–95, (2000).

Stallings-Mann et al., Alternative splicing of exon 3 of the human growth hormone receptor is the result of an unusual genetic polymorphism. Proc Natl Acad Sci USA 93:12394–9, (1996).

Strausberg, R. EST Accession No. BE795492; BE791829; BE791472

Wang et al., C-CAM1, a candidate tumor suppressor gene, is abnormally expressed in primary lung cancers. Clin Cancer Res 6:2988–93, (2000).

Yamaguchi et al., Overexpression of the Csk homologous kinase (Chk tyrosine kinase) induces multinucleation: a possible role for chromosome-associated Chk in chromosome dynamics. J Cell Sci 114:1631–41, (2001).

Yamashita et al., The Csk homologous kinase associates with TrkA receptors and is involved in neurite outgrowth of PC12 cells. J Biol Chem 274:15059–65, (1999).

Zrihan-Licht et al., Csk homologous kinase, a novel signaling molecule, directly associates with the activated ErbB-2 receptor in breast cancer cells and inhibits their proliferation. J Biol Chem 273:4065–72, (1998).

---

What is claimed is:

1. An isolated nucleic acid encoding the polypeptide comprising the amino acid sequence of SEQ ID NO: 2.

2. The isolated nucleic acid of claim 1, which comprises the nucleotide sequence of SEQ ID NO: 1.

3. An expression vector comprising the nucleic acid of claim 1.

4. A host cell transformed with the expression vector of claim 3.

* * * * *

SEQUENCE LISTING

```
<160> NUMBER OF SEQ ID NOS: 2

<210> SEQ ID NO 1
<211> LENGTH: 2065
<212> TYPE: DNA
<213> ORGANISM: Homo sapiens
<220> FEATURE:
<221> NAME/KEY: CDS
<222> LOCATION: (263)..(1921)
<223> OTHER INFORMATION:

<400> SEQUENCE: 1
ggagcaactc gctccaagtt gtgcagccgg gaccgcctcg gggtgtgcag ccggctcgcg      60
gaggccctcc tgggggcggg cggggcgcgg ctcggggcg cccctgagc agaaaacagg      120 aagaaccagg ctcggtccag tggcacccag ctccctacct cctgtgccag ccgcctggcc     180
tgtggcaggc cattcccagc gtccccgact gtgaccactg gctcagtgtg cctctcacct     240
gcctcagttt cctctggggg cg atg gcg ggg cga ggc tct ctg gtt tcc tgg      292
                        Met Ala Gly Arg Gly Ser Leu Val Ser Trp
                         1               5                  10 cgg gca ttt cac ggc tgt gat tct gct gag gaa ctt ccc cgg gtg agc      340
Arg Ala Phe His Gly Cys Asp Ser Ala Glu Glu Leu Pro Arg Val Ser
             15                  20                  25 ccc cgc ttc ctc cga gcc tgg cac ccc cct ccc gtc tca gcc agg atg      388
Pro Arg Phe Leu Arg Ala Trp His Pro Pro Val Ser Ala Arg Met
             30                  35                  40 cca acg agg cgc tgg gcc ccg ggc acc cag tgt atc acc aaa tgc gag      436
Pro Thr Arg Arg Trp Ala Pro Gly Thr Gln Cys Ile Thr Lys Cys Glu
         45                  50                  55
```

-continued

```
cac acc cgc ccc aag cca ggg gag ctg gcc ttc cgc aag ggc gac gtg       484
His Thr Arg Pro Lys Pro Gly Glu Leu Ala Phe Arg Lys Gly Asp Val
    60                  65                  70 gtc acc atc ctg gag gcc tgc gag aac aag agc tgg tac cgc gtc aag       532
Val Thr Ile Leu Glu Ala Cys Glu Asn Lys Ser Trp Tyr Arg Val Lys
75                  80                  85                  90 cac cac acc agt gga cag gag ggg ctg ctg gca gct ggg gcg ctg cgg       580
His His Thr Ser Gly Gln Glu Gly Leu Leu Ala Ala Gly Ala Leu Arg
                95                  100                 105 gac ggg gag gcc ctc tcc gca gac ccc aag ctc agc ctc atg ccg tgg       628
Asp Gly Glu Ala Leu Ser Ala Asp Pro Lys Leu Ser Leu Met Pro Trp
            110                 115                 120 ttc cac ggg aag atc tcg ggc cag gag gct gtc cag cag ctg cag cct       676
Phe His Gly Lys Ile Ser Gly Gln Glu Ala Val Gln Gln Leu Gln Pro
        125                 130                 135 ccc gag gat ggg ctg ttc ctg gtg cgg gag tcc gcg cgc cac ccc ggc       724
Pro Glu Asp Gly Leu Phe Leu Val Arg Glu Ser Ala Arg His Pro Gly
    140                 145                 150 gac tac gtc ctg tgc gtg agc ttt ggc cgc gac gtc atc cac tac cgc       772
Asp Tyr Val Leu Cys Val Ser Phe Gly Arg Asp Val Ile His Tyr Arg
155                 160                 165                 170 gtg ctg cac cgc gac ggc cac ctc aca atc gat gag gcc gtg ttc ttc       820
Val Leu His Arg Asp Gly His Leu Thr Ile Asp Glu Ala Val Phe Phe
                175                 180                 185 tgc aac ctc atg gac atg gtg gag agg cca ccc ggg aac gga aca gga       868
Cys Asn Leu Met Asp Met Val Glu Arg Pro Pro Gly Asn Gly Thr Gly
            190                 195                 200 tgc tgg ggt tcc cct ccc tgg ggc tgg gct cat ggc tgt ccc acc atc       916
Cys Trp Gly Ser Pro Pro Trp Gly Trp Ala His Gly Cys Pro Thr Ile
        205                 210                 215 ctg cag cat tac agc aag gac aag ggc gct atc tgc acc aag ctg gtg       964
Leu Gln His Tyr Ser Lys Asp Lys Gly Ala Ile Cys Thr Lys Leu Val
    220                 225                 230 aga cca aag cgg aaa cac ggg acc aag tcg gcc gag gag gag ctg gcc      1012
Arg Pro Lys Arg Lys His Gly Thr Lys Ser Ala Glu Glu Glu Leu Ala
235                 240                 245                 250 agg gcg ggc tgg tta ctg aac ctg cag cat ttg aca ttg gga gca cag      1060
Arg Ala Gly Trp Leu Leu Asn Leu Gln His Leu Thr Leu Gly Ala Gln
                255                 260                 265 atc gga gag gga gag ttt gga gct gtc ctg cag ggt gag tac ctg ggg      1108
Ile Gly Glu Gly Glu Phe Gly Ala Val Leu Gln Gly Glu Tyr Leu Gly
            270                 275                 280 caa aag gtg gcc gtg aag aat atc aag tgt gat gtg aca gcc cag gcc      1156
Gln Lys Val Ala Val Lys Asn Ile Lys Cys Asp Val Thr Ala Gln Ala
        285                 290                 295 ttc ctg gac gag acg gcc gtc atg acg aag atg caa cac gag aac ctg      1204
Phe Leu Asp Glu Thr Ala Val Met Thr Lys Met Gln His Glu Asn Leu
    300                 305                 310 gtg cgt ctc ctg ggc gtg atc ctg cac cag ggg ctg tac att gtc atg      1252
Val Arg Leu Leu Gly Val Ile Leu His Gln Gly Leu Tyr Ile Val Met
315                 320                 325                 330 gag cac gtg agc aag ggc aac ctg gtg aac ttt ctg cgg acc cgg ggt      1300
Glu His Val Ser Lys Gly Asn Leu Val Asn Phe Leu Arg Thr Arg Gly
                335                 340                 345 cga gcc ctc gtg aac acc gct cag ctc ctg cag ttt tct ctg cac gtg      1348
Arg Ala Leu Val Asn Thr Ala Gln Leu Leu Gln Phe Ser Leu His Val
            350                 355                 360 gcc gag ggc atg gag tac ctg gag agc aag aag ctt gtg cac cgc gac      1396
Ala Glu Gly Met Glu Tyr Leu Glu Ser Lys Lys Leu Val His Arg Asp
```

-continued

```
                  365                 370                 375
ctg gcc gcc cgc aac atc ctg gtc tca gag gac ctg gtg gcc aag gtc    1444
Leu Ala Ala Arg Asn Ile Leu Val Ser Glu Asp Leu Val Ala Lys Val
    380                 385                 390 agc gac ttt ggc ctg gcc aaa gcc gag cgg aag ggg cta gac tca agc    1492
Ser Asp Phe Gly Leu Ala Lys Ala Glu Arg Lys Gly Leu Asp Ser Ser
395                 400                 405                 410 cgg ctg ccc gtc aag tgg acg gcg ccc gag gct ctc aaa cac ggg ttc    1540
Arg Leu Pro Val Lys Trp Thr Ala Pro Glu Ala Leu Lys His Gly Phe
                415                 420                 425 acc agc aag tcg gat gtc tgg agt ttt ggg gtg ctg ctc tgg gag gtc    1588
Thr Ser Lys Ser Asp Val Trp Ser Phe Gly Val Leu Leu Trp Glu Val
                430                 435                 440 ttc tca tat gga cgg gct ccg tac cct aaa atg tca ctg aaa gag gtg    1636
Phe Ser Tyr Gly Arg Ala Pro Tyr Pro Lys Met Ser Leu Lys Glu Val
                445                 450                 455 tcg gag gcc gtg gag aag ggg tac cgc atg gaa ccc ccc gag ggc tgt    1684
Ser Glu Ala Val Glu Lys Gly Tyr Arg Met Glu Pro Pro Glu Gly Cys
    460                 465                 470 cca ggc ccc gtg cac gtc ctc atg agc agc tgc tgg gag gca gag ccg    1732
Pro Gly Pro Val His Val Leu Met Ser Ser Cys Trp Glu Ala Glu Pro
475                 480                 485                 490 ccc gcc ggc cac cct tcc gca aac tgg ccg aga agc tgg ccc ggg agc    1780
Pro Ala Gly His Pro Ser Ala Asn Trp Pro Arg Ser Trp Pro Gly Ser
                495                 500                 505 tac gca gtg cag gtg ccc cag cct ccg tct cag ggc agg acg ccg acg    1828
Tyr Ala Val Gln Val Pro Gln Pro Pro Ser Gln Gly Arg Thr Pro Thr
                510                 515                 520 gtc cac ctc gcc ccg aag cca gga gcc ctg acc cca ccc ggt ggc cct    1876
Val His Leu Ala Pro Lys Pro Gly Ala Leu Thr Pro Pro Gly Gly Pro
                525                 530                 535 tgg ccc cag agg acc gag aga gtg gag agt gcg gcg tgg ggg cac        1921
Trp Pro Gln Arg Thr Glu Arg Val Glu Ser Ala Ala Trp Gly His
            540                 545                 550 tgaccaggcc caaggagggt ccaggcgggc aagtcatcct cctggtgccc acagcagggg  1981
ctggcccacg tagggggctc tgggcggccc gtggacaccc agacctgcg aaggatgatc   2041 gcccgataaa gacggattct aagg                                         2065
```

<210> SEQ ID NO 2
<211> LENGTH: 553
<212> TYPE: PRT
<213> ORGANISM: Homo sapiens

<400> SEQUENCE: 2

```
Met Ala Gly Arg Gly Ser Leu Val Ser Trp Arg Ala Phe His Gly Cys
1               5                   10                  15

Asp Ser Ala Glu Glu Leu Pro Arg Val Ser Pro Arg Phe Leu Arg Ala
            20                  25                  30

Trp His Pro Pro Pro Val Ser Ala Arg Met Pro Thr Arg Arg Trp Ala
        35                  40                  45

Pro Gly Thr Gln Cys Ile Thr Lys Cys Glu His Thr Arg Pro Lys Pro
    50                  55                  60

Gly Glu Leu Ala Phe Arg Lys Gly Asp Val Val Thr Ile Leu Glu Ala
65                  70                  75                  80

Cys Glu Asn Lys Ser Trp Tyr Arg Val Lys His His Thr Ser Gly Gln
                85                  90                  95

Glu Gly Leu Leu Ala Ala Gly Ala Leu Arg Asp Gly Glu Ala Leu Ser
```

```
                100                 105                 110
Ala Asp Pro Lys Leu Ser Leu Met Pro Trp Phe His Gly Lys Ile Ser
            115                 120                 125
Gly Gln Glu Ala Val Gln Gln Leu Gln Pro Pro Glu Asp Gly Leu Phe
            130                 135                 140
Leu Val Arg Glu Ser Ala Arg His Pro Gly Asp Tyr Val Leu Cys Val
145                 150                 155                 160
Ser Phe Gly Arg Asp Val Ile His Tyr Arg Val Leu His Arg Asp Gly
                165                 170                 175
His Leu Thr Ile Asp Glu Ala Val Phe Phe Cys Asn Leu Met Asp Met
            180                 185                 190
Val Glu Arg Pro Pro Gly Asn Gly Thr Gly Cys Trp Gly Ser Pro Pro
            195                 200                 205
Trp Gly Trp Ala His Gly Cys Pro Thr Ile Leu Gln His Tyr Ser Lys
    210                 215                 220
Asp Lys Gly Ala Ile Cys Thr Lys Leu Val Arg Pro Lys Arg Lys His
225                 230                 235                 240
Gly Thr Lys Ser Ala Glu Glu Leu Ala Arg Ala Gly Trp Leu Leu
                245                 250                 255
Asn Leu Gln His Leu Thr Leu Gly Ala Gln Ile Gly Glu Gly Glu Phe
            260                 265                 270
Gly Ala Val Leu Gln Gly Glu Tyr Leu Gly Gln Lys Val Ala Val Lys
            275                 280                 285
Asn Ile Lys Cys Asp Val Thr Ala Gln Ala Phe Leu Asp Glu Thr Ala
            290                 295                 300
Val Met Thr Lys Met Gln His Glu Asn Leu Val Arg Leu Leu Gly Val
305                 310                 315                 320
Ile Leu His Gln Gly Leu Tyr Ile Val Met Glu His Val Ser Lys Gly
                325                 330                 335
Asn Leu Val Asn Phe Leu Arg Thr Arg Gly Arg Ala Leu Val Asn Thr
            340                 345                 350
Ala Gln Leu Leu Gln Phe Ser Leu His Val Ala Glu Gly Met Glu Tyr
            355                 360                 365
Leu Glu Ser Lys Lys Leu Val His Arg Asp Leu Ala Ala Arg Asn Ile
            370                 375                 380
Leu Val Ser Glu Asp Leu Val Ala Lys Val Ser Asp Phe Gly Leu Ala
385                 390                 395                 400
Lys Ala Glu Arg Lys Gly Leu Asp Ser Ser Arg Leu Pro Val Lys Trp
                405                 410                 415
Thr Ala Pro Glu Ala Leu Lys His Gly Phe Thr Ser Lys Ser Asp Val
            420                 425                 430
Trp Ser Phe Gly Val Leu Leu Trp Glu Val Phe Ser Tyr Gly Arg Ala
        435                 440                 445
Pro Tyr Pro Lys Met Ser Leu Lys Glu Val Ser Glu Ala Val Glu Lys
        450                 455                 460
Gly Tyr Arg Met Glu Pro Pro Glu Gly Cys Pro Gly Pro Val His Val
465                 470                 475                 480
Leu Met Ser Ser Cys Trp Glu Ala Glu Pro Ala Gly His Pro Ser
                485                 490                 495
Ala Asn Trp Pro Arg Ser Trp Pro Gly Ser Tyr Ala Val Gln Val Pro
            500                 505                 510
Gln Pro Pro Ser Gln Gly Arg Thr Pro Thr Val His Leu Ala Pro Lys
            515                 520                 525
```

```
Pro Gly Ala Leu Thr Pro Pro Gly Gly Pro Trp Pro Gln Arg Thr Glu
    530                 535                 540

Arg Val Glu Ser Ala Ala Trp Gly His
545                 550
```